United States Patent [19]

Lee

[11] Patent Number: 5,019,045
[45] Date of Patent: May 28, 1991

[54] HYPODERMIC SYRINGE WITH A LOCKING NEEDLE ASSEMBLY AND SYRINGE COMBINATION

[76] Inventor: Sang D. Lee, 394 Lawton St., Cliffside Park, N.J. 07010

[21] Appl. No.: 328,165

[22] Filed: Mar. 24, 1989

[51] Int. Cl.⁵ .............................................. A61M 5/00
[52] U.S. Cl. .................... 604/110; 604/240; 604/218
[58] Field of Search ............... 604/110, 181, 182, 183, 604/186, 187, 210, 244, 220, 221, 240–243

[56] References Cited

U.S. PATENT DOCUMENTS

| | | | |
|---|---|---|---|
| 1,668,315 | 5/1928 | Hein | 604/241 |
| 2,764,978 | 10/1956 | Everett | 604/242 |
| 3,402,713 | 9/1968 | Benkowski et al. | 604/241 |
| 4,391,272 | 7/1985 | Staempfli | 604/110 |
| 4,493,703 | 1/1975 | Butterfield | 604/110 |
| 4,496,344 | 1/1985 | Kamstra | 604/90 |
| 4,563,174 | 1/1986 | Dupont et al. | 604/89 |
| 4,781,684 | 11/1988 | Trenner | 604/110 |
| 4,820,272 | 4/1989 | Palmer | 604/110 |
| 4,826,483 | 5/1989 | Molnar | 604/110 |
| 4,826,490 | 5/1989 | Byrne et al. | 604/110 |
| 4,883,466 | 11/1989 | Gloriet | 604/110 |

FOREIGN PATENT DOCUMENTS

| | | | |
|---|---|---|---|
| 8802640 | 4/1988 | PCT Int'l Appl. | 604/110 |
| 8904187 | 5/1989 | PCT Int'l Appl. | 604/110 |

Primary Examiner—C. Fred Rosenbaum
Assistant Examiner—Kathleen Daley
Attorney, Agent, or Firm—Handal & Morofsky

[57] ABSTRACT

A needle assembly and syringe combination that are permanently joined through a mechanical locking arrangement of a groove 32, catch space 34 and catch 36 is disclosed. The use of this locking arrangement on a non-reusable syringe renders the needle 20 unusable along wih the syringe after a single use.

19 Claims, 5 Drawing Sheets

HYPODERMIC SYRINGE WITH A LOCKING NEEDLE ASSEMBLY AND SYRINGE COMBINATION

CROSS-REFERENCE TO RELATED APPLICATIONS

This application is a continuation-in-part of co-pending U.S. patent application Ser. No. 173,827, still pending, of Sang Don Lee, filed Mar. 28, 1988 and entitled "Method and Apparatus for Improved Hypodermic Syringe" the disclosure of which is incorporated herein by reference.

TECHNICAL FIELD

The present invention relates to disposable hypodermic needles which are rendered useless after a single use through a locking mechanism which is engaged when the hypodermic needle is connected to a non-reusable syringe Such a locking system, comprising a needle assembly and the syringe constructed to engage such a needle assembly, is an improvement upon the non-reusable syringe alone.

BACKGROUND

The increasing use of disposable syringes and needles and the prevention of the reuse of this equipment has become an important health issue as diseases, and, in particular, incurable and sometimes fatal diseases such as hepatitis and acquired immune deficiency syndrome (AIDS), spread by used equipment persist and grow.

Originally the hypodermic needle was reusable, requiring sterilization between each use and occasional resharpening. The number of needles disposed of was therefore very low and the needles were only disposed of because the usable life of the needle had been reached. Control over reusable needles could be kept very strict, and doctor and nurse regularly sterilize their needles. Nevertheless, in a number of cases, needles were believed to be a means of spreading infection.

Today, in effort to reduce spread of infection needles are disposed of after one use, and in an unsterile condition. The numbers of needles used makes control over them very difficult as large supplies of the packaged sterile needles are kept on hand and the used needles, quite capable of being reused, are simply disposed of with little or no afterthought.

It is the disposed-of needles that often end up in the hands of illicit drug users. The needles are obtained in a contaminated condition and each reuse further contaminates the needle.

The contaminants found include biologically active contaminants such as viruses. Hepatitis has long been associated with intravenous drug users. However, today attention has been focused upon the spread of HIV (Human Immune Virus), associated with AIDS, through the intravenous drug community.

Methods of preventing the reuse of a syringe have been proposed. However, needles may still be removed from these syringes and the needles then reused.

Syringes may be fabricated from eyedroppers, from pipettes and rubber bulbs or other materials. The requirement of a needle for intravenous introduction of a substance does not allow such freedom in substitution or fabrication.

In the past doctors, nurses and those others that would use disposable needles have deliberately blunted or broken the needles before disposing of them. However, not all needle users performed this precaution and those performing it may not do so in every case. Since this requires an additional step, it is easy to grow lax. The number of needles in use by so many professionals also leads to a more casual manner in disposal of the needles.

The availability of needles, much more so than syringes, is a factor in the spread of life threatening diseases and the reuse of disposable needles has proven to be a large factor in the availability of needles.

SUMMARY OF THE INVENTION

The invention is intended to provide a remedy to both the problems of illicit reuse of a contaminated syringe and unnecessary movement of the driver within the body of syringe eliminating possible discomfort during injections.

The use of a locking device within the body of the syringe to prevent the withdrawal of the plunger/driver assembly once it has passed a given point renders the syringe of this invention inoperable after a single use. Therefore the problem of reuse of a contaminated syringe is overcome by this invention.

The locking comes about through the engagement of a specially designed driver with the locking means associated with the interior surface of the syringe body.

The utilization of an oval body with a plunger and driver of a like configuration will prevent any rotation of the driver within the body of the syringe and tend to limit the play or wobble of the plunger within the syringe. This shape will therefore limit movements that may be transferred to the needle which in turn may cause discomfort or pain to the person receiving the injection.

The oval shape of the syringe will provide stability in another form in that an oval body will fit more comfortably and securely between the fingers of the professional administering the injection.

The oval shape, in preventing rotation of the driver, also maintains the proper alignment of the engagement features of the driver to the locking units on the interior body wall assuring the proper functioning of the inventive syringe.

The invention is also intended to provide a remedy to the problems posed by disposable needles. By providing a locking mechanism at the point where the needle assembly engages the syringe, the removal of the needle from the syringe may be prevented. In the case of an otherwise conventional syringe, the needle may be reused along with the syringe even though the needle may not be removed from the syringe.

The invention contemplates a locking mechanism to act between a needle assembly and a non-reusable syringe such as that disclosed in the parent application. In this combination neither the syringe nor the needle are reusable. In this situation the needle is permanently affixed to the non-working syringe so it may not be used with or apart from the syringe.

The needle is separately packaged in order to allow the selection of the needle size when an injection is to be performed. The needle assembly is then engaged with the syringe and the locking of the assembly to the syringe occurs when the needle assembly is functionally engaged or before. No adhesive is used, the locking is mechanical. The presence of adhesive, bonding or other material presents sterilization problems and environmental heat is detrimental to the bonding function of these materials.

BRIEF DESCRIPTION OF THE DRAWINGS

One way of carrying out the invention is described in detail below with reference to drawings which illustrate only a few specific embodiments of the invention and in which.

DETAILED DESCRIPTION OF THE DRAWINGS

Figure 1:
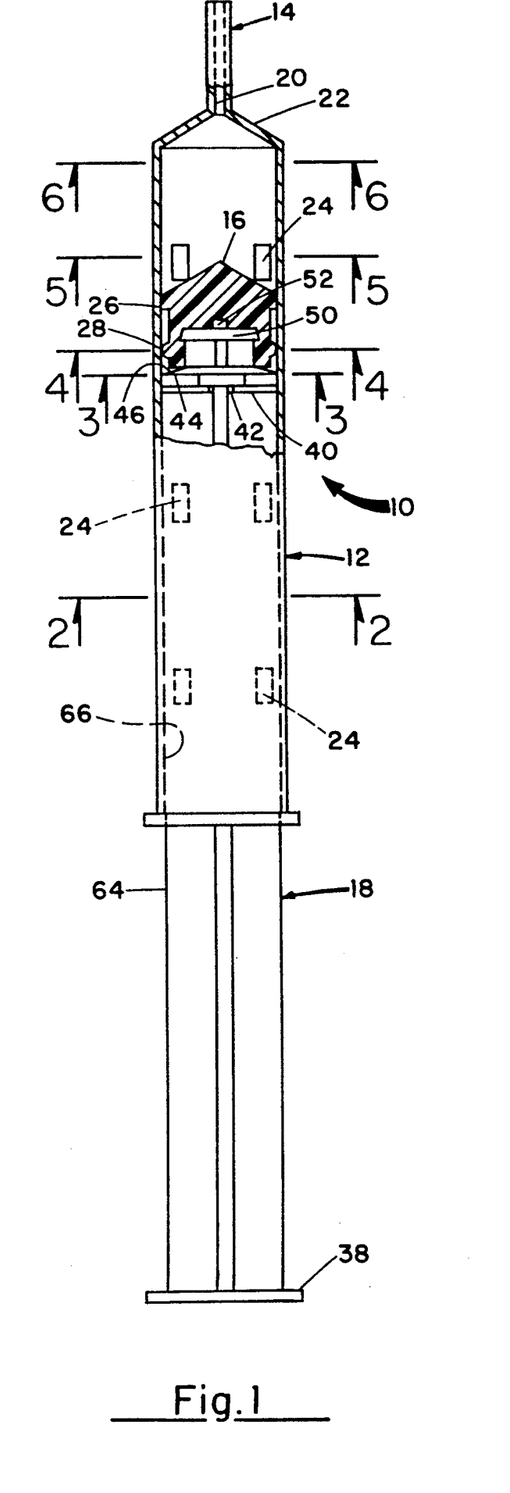
FIG. 1 is a plan view, partially in cutaway and partially in cross-section of a hypodermic syringe constructed in accordance to the present invention.

Referring to FIG. 1, a hypodermic needle or syringe, 10, constructed in accordance with the present invention, is illustrated. Syringe 10 comprises a body portion 12 a needle support 14 a rubber plunger 16 and a driver 18.

Support 14 includes an inner channel 20 for passing a medicinal fluid carried within the interior volume defined by body 12. A tapered portion 22 gradually connects the front of body portion 12 to needle support 14.

Figure 2:
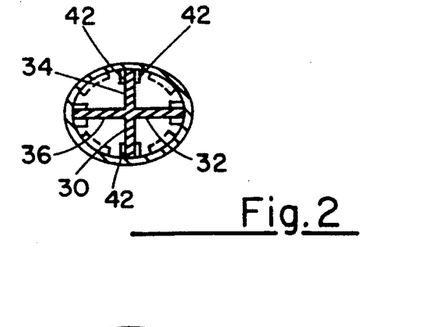
FIG. 2 is a cross-sectional view of the inventive hypodermic syringe along line 2—2 of FIG. 1.
Figure 3:
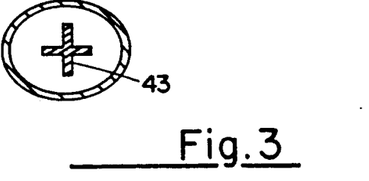
FIG. 3 is a cross-sectional view of the inventive hypodermic syringe along line 3—3 of FIG. 1.
Figure 8:
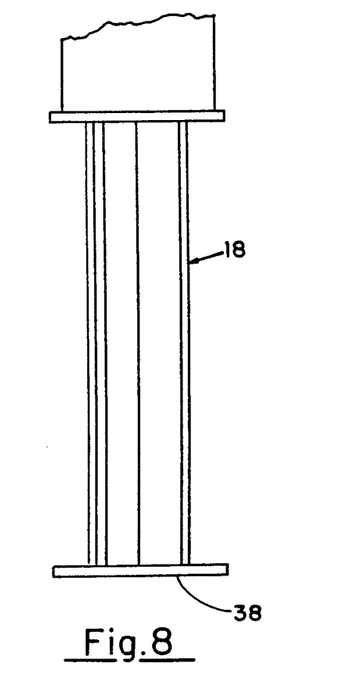
FIG. 8 is a view along line 8—8 of FIG. 5 and illustrates a first stage in the emptying and locking of inventive hypodermic syringe.

A plurality of locking stops 24 are provided on the inside walls on body portion 12. Plunger 16 includes circumferential ribs 26 and 28. A driver 18 comprising four mutually perpendicular beams 30, 32, 34 and 36, as illustrated in FIG. 2 is provided with a comfortable flat receiving pad 38 (FIG. 8). At the opposite end of beams 30-36 is a slotted base pad 40 which includes slots 42. A coupling comprising a cross-shape support member 43 is formed integrally with the beams 30-36 and pad 38 as well as tapered base 44 which include annular conical ramped surface 46.

Figure 4:
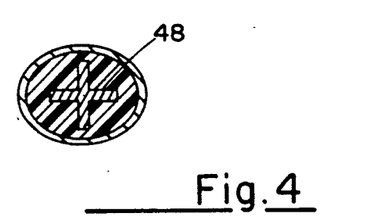
FIG. 4 is a cross-sectional view of the inventive hypodermic syringe along line 4—4 of FIG. 1.

Finally, the driver is completed by a plunger support structure comprising a cross-shape plunger support 48, shown in FIG. 4, a disc 50, and a nub 52 all of which are formed integrally in a single injection molding operation with the rest of driver 18.

Figure 5:
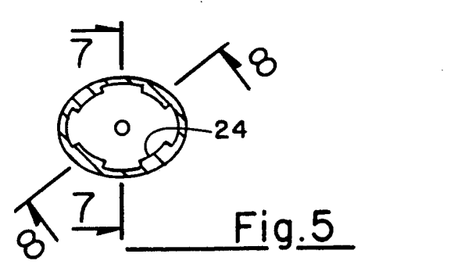
FIG. 5 is a cross-sectional view of the inventive hypodermic syringe along line 5—5 FIG. 1.

As shown in FIG. 5, locking stops 24 extend over a portion of the circumference of the inner wall of body portion 12 and are positioned in such a manner that beams 30-36 may pass between them, as illustrated in FIG. 2.

Figure 6:
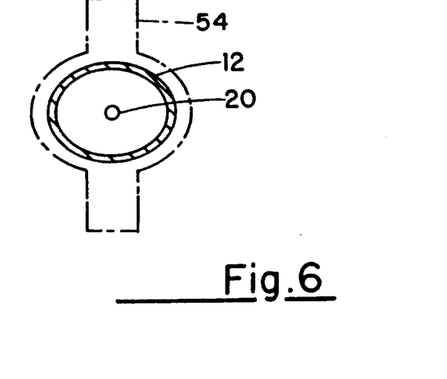
FIG. 6 is a cross-sectional view of the inventive hypodermic syringe along line 6—6 of FIG. 1.
Figure 7:
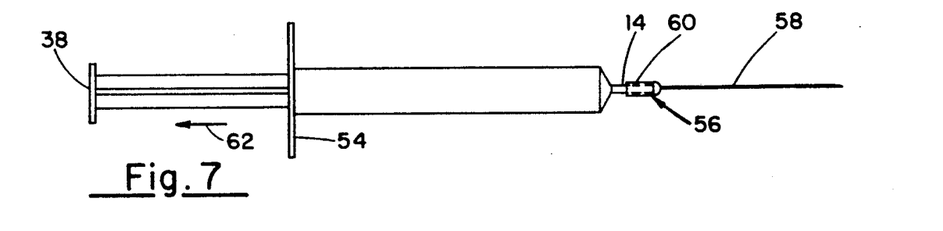
FIG. 7 is a plan view of the inventive hypodermic syringe with a needle element in place.

As can be seen from FIGS. 1 and 6 inner channel 20 is in communication with the interior volume of body portion 12. As shown in FIG. 7, the syringe 10 is completed by middle finger and index finger engaging tips 54. In practice the syringe would not be used before the selection and mounting of an appropriate needle assembly 56 comprising a needle 58 of an appropriate diameter and length depending upon the location of the injection and the nature of the medication and a mounting 60 which mates with the tip of needle support 14. After mounting an appropriate needle the doctor would take the syringe, substantially as shown in a position illustrated in FIG. 1 except with the needle attached as illustrated in FIG. 7 and plunge the needle 58 into a bottle of medication The driver would then be withdrawn in the direction indicated by arrow 62 and the medication thus drawn by vacuum into the interior volume of body portion 12. The physician then, in a conventional matter, depresses driver 18 with the syringe aimed upwardly in order to exclude the air which, naturally, has risen to the top of the syringe. The needle may now be inserted into the site of injection and advanced in order to deliver the medicinal fluid from the syringe into the patient. During such advancement of the driver, it is noted that the closed fitting relationship between the edges 64 of the driver and the inner sidewalls 66 of the body portion 12 results in minimal angular relative movement between driver 18 and body portion 12. In addition, because body portion 12 is of a elliptical cross-section, and has inner walls which conform to the outer walls of plunger 16, rotational movement during operation of the inventive syringe is also prevented. These two factors combine to increase the comfort of the device for the patient.

Figure 9:
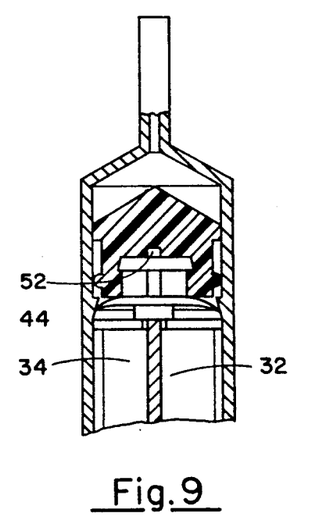
FIGS. 9-11 are partially cut away views with the rubber plunger shown in cross-section similar to FIG. 8 and illustrating the second, third, and fourth stages in the locking of the inventive hypodermic syringe.
Figure 10:
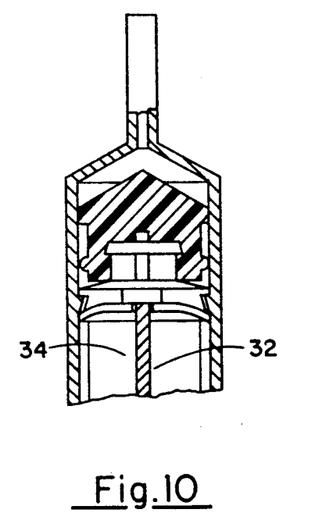

As the syringe is being used and gradually emptied of the medication or other fluid contained within a body portion 12, the plunger 16 eventually advances to the position shown in FIG. 8. Continued operation of the syringe results in advancement to the position illustrated in FIG. 9. Here annular surface 46 begins to bear against stops 24, resulting in flexure of base 44. As the needle is continued to be operated, the base 44 passes over the forward surface 68 (FIG. 8) of stops 24 and assumes the position shown in FIG. 10. At this point the continued advancement of driver 18 has resulted in urging base pad 40 against the ramp surface 70 of stops 24 thus resulting in flexure of pad 40. Flexure of pad 40 is accommodated by slots 42 shown in FIGS. 1 and 2 provided along side of each of the beams 30–36. It is also possible to include additional stops 24 as shown in phantom lines in FIG. 1.

Figure 11:
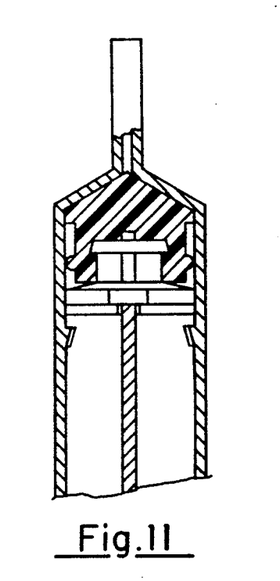
Figure 12:
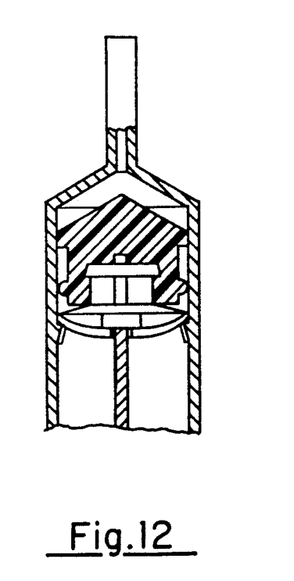
FIG. 12 illustrates the locked position of the inventive hypodermic syringe when a force is applied in an attempt to reuse it.

Continued operation of the syringe finally results in achieving the position illustrated in FIG. 11 where both the pad and the base have advanced into the lock position. Any attempt to remove the syringe will not be successful insofar as slight flexure of base 40 will result in the necessity of forcing both the base pad 40 and base 44 against surfaces 68 of stops 24. While the materials of base pad 40 and base 44 are flexible, the combined thicknesses of the two is practically unyielding so as not to allow removal or dislodging of the plunger and driver 18. This is in contrast to the advance of the plunger where in the base pad and base are individually and gradually flexed as they separately encounter and pass over the ramp surface 70.

While a wide range of available materials may suggest different dimensions for various parts of the inventive syringe using conventional syringe manufacturing materials, the preferred embodiment contemplates the dimensions listed below.

The stops 24 are to be 4 mm in length and over this length gradually rise to a height of 1 mm from the inner surface 66 of the body portion 12. Four stops are used (one in each section formed by adjacent beams 30–36).

The slotted base pad 40 is of the same basic shape and dimensions as the interior area defined by a cross-section of the body 12 as shown in FIG. 2. The slots 42 on the slotted base pad 40 are to be adjacent to, and on each side of, beams 30–36 and to extend inward alongside said beams 1 mm. The slots are to be 0.3 mm in width. The thickness of this slotted base pad 40 is 1 mm.

The distance between the slotted base pad 40 and the tapered base 44 is 0.5 mm. The tapered base is 1.5 mm in thickness. The annular conical ramped surface 46 varies from a dimension the same as that of slotted base pad 40 (on the side adjacent to said slotted base pad 40) to a size such that the outer edge on the side adjacent to the rubber plunger 16 is at least 1 mm away from the inner surface 66 of the body portion 12.

The leading end of the rubber plunger 16 is designed to conform to the tapered portion 22 and the cylindrical body of the rubber plunger 16 is to be 7 mm in length.

The beams 30–36 are 1.5 mm thickness. The pad 38 is 1.5 mm in thickness and the finger engaging tips 54 are 2 mm in thickness.

These dimensions are for a standard 5 cc syringe

Rubber plunger body 16 is molded to tightly conformed to the plunger support.

Figure 13:
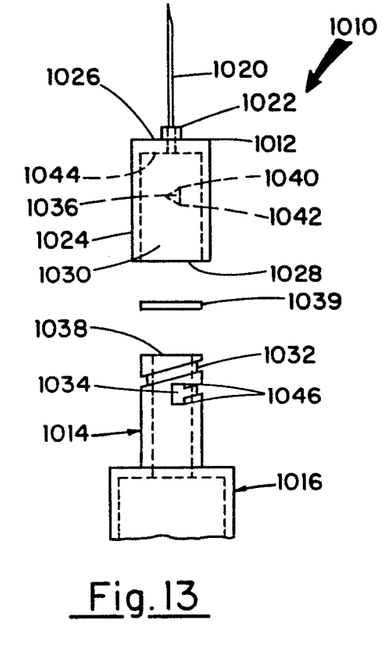
FIG. 13 is a side view of a needle support and needle assembly illustrating the locking mechanism.

The inventive apparatus 1010 consists of a needle assembly 1012 and the needle support 1014. The needle support is part of a syringe body 1016. Needle assembly 1012 comprises a needle 1020 held by an annular seal 1022. Seal 1022 is in turn held by a needle assembly body 1024 substantially closed at end 1026 and open at end 1028. The internal diameter of open end 1028 is substantially the same as the outside diameter of needle support 1014 and permits the entry of the needle support into the cavity 1030 of needle assembly body 1024.

Needle support 1014 contains a helical groove 1032 that terminates in a catch space 1034. Needle assembly 1012 has, on the internal wall, defining cavity 1030, a wedge-shaped catch 1036.

The needle assembly may be fitted upon the needle support and the needle support will enter cavity 1030. Needle support 1014 may be inserted until top edge 1038 abuts catch 1036 within the needle assembly Rotation of the needle assembly with respect to the needle support will bring about an alignment such that catch 1036 will engage the top of helical groove 1032. Continued rotation combined with a force driving the needle support into the needle assembly will result in the wedge-shaped catch entering the groove and undergoing compression as the groove is dimensioned such that with width of groove 1032 is less than the distance between tips 1040 and 1042 on catch 1036. Tips 1040 and 1042 are forced closer together upon entering the groove.

Rotation is continued until catch 1036 reaches catch space 1034 marking the end of the groove. Upon catch 1036 reaching catch area 1034 needle assembly 1012 is functionally engaged with needle support 1014 and therefore also to the syringe body 1016. Interior end wall 1044 of the needle assembly is in forced contact with top edge 1038 of the needle support. A washer or other sealing device 1039 may be in forced contact, between, and with both interior end wall 1044 and top edge 1038.

Upon reaching and entering catch area 1034 the tips of catch 1036 are no longer under compression and therefore the tips return to the relative positions they held before compression. The distance between tips 1040 and 1042 is now, once again, greater than the width of groove 1032. The face of the wedge, between tips 1040 and 1042, contacts surface 1046 within the catch space and prevents reentry of wedge-shaped catch 1036 into groove 1032, thus preventing removal of the needle assembly from the needle support.

Figure 14:
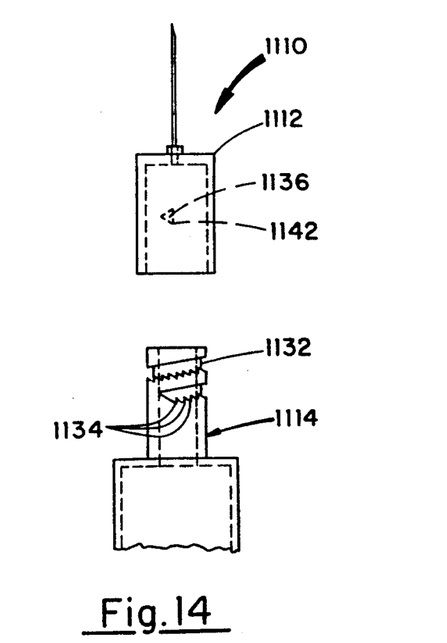
FIG. 14 is a side view depicting an alternate embodiment of the locking mechanism.

An alternative embodiment of the locking mechanism is illustrated in FIG. 14. The inventive apparatus 1110 again consists of a needle assembly 1112 with a catch 1136 and a needle support 1114 with a groove 1132. However, instead of a single catch space there are many catch spaces 1134 arranged along with entire length of groove 1132. In this embodiment tip 1142 of catch 1136 undergoes compression and engages with catch 1134 by returning to its original shape after compression is removed. The serrated groove and the wedge act as a ratchet and pawl. This embodiment maintains the needle assembly - needle support connection through locking even before a functional engagement is achieved.

Figures 15, 16, 17:
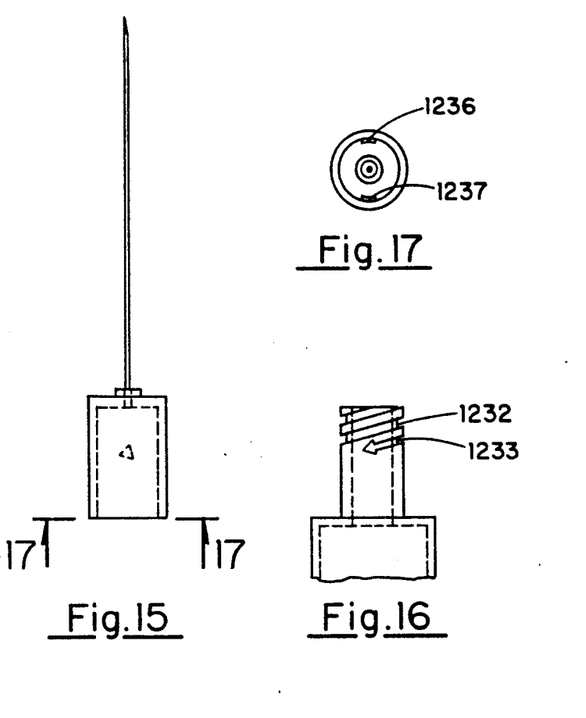
FIG. 15 is a side view of a needle assembly with a further embodiment of the locking mechanism.
FIG. 16 is a side view of the needle support for the needle assembly of FIG. 15.
FIG. 17 is a bottom view of the needle assembly of FIG. 15 taken along line 17—17.

FIGS. 15, 16 and 17 illustrate a double-threaded version of the invention. Two grooves, 1232 and 1233 engage two catches 1236 and 1237. The twist on method of engagement of the locking mechanism operates as in the previous embodiments.

Figure 18:
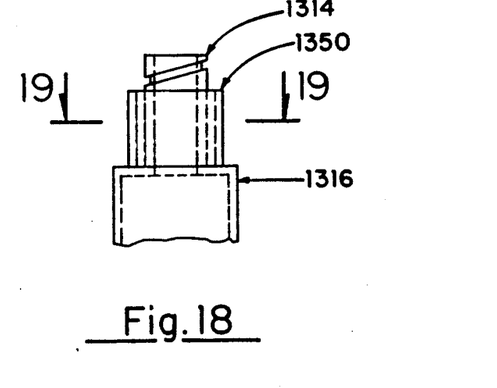
FIG. 18 is a side view of an embodiment of a needle support with a support ring.
Figure 19:
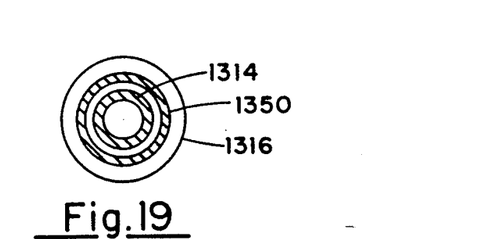
FIG. 19 is a sectional view of the needle support of FIG. 18 taken along the line 19—19.

FIGS. 18 and 19 illustrate the inventive device in an embodiment incorporating a securing collar. Securing collar 1350 extends from circular syringe body 1316 and is coaxial with needle support 1314. The difference between the inside diameter of securing collar 1350 and the outside diameter of needle support 1314 is substantially the same as the thickness of the wall of a needle assembly body, the needle assembly body wall will be in a position between the securing collar and the needle support when functionally engaged.

Figure 20:
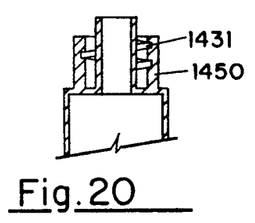
FIG. 20 is a sectional view of an alternative embodiment of a needle support with a support ring.
Figure 21:
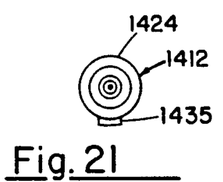
FIG. 21 is a bottom view of a needle assembly compatible with the needle support shown in FIG. 8.

A securing collar may be configured to have an active part in the locking action, as illustrated in FIGS. 20 and 21. A groove 1431 is included in securing collar 1450. Catch 1435 is positioned on the exterior of body 1424 of needle assembly 1412.

Figure 22:
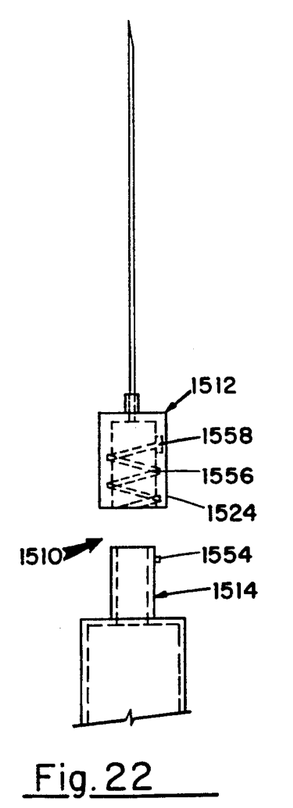
FIG. 22 is a side view of a still further embodiment of the locking mechanism.

The groove used in the inventive locking system between the needle assembly and needle support need not be restricted to syringe extensions, but may be incorporated into the needle support. Apparatus 1510, illustrated in FIG. 22, has catch 1554 positioned on needle support 1514, accordingly groove 1556 is within body 1524 of needle assembly 1512. Catch space 1558 terminates groove 1556.

Figure 23:
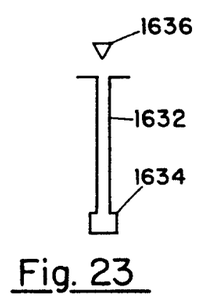
FIGS. 23-25 schematically depict various groove and catch combinations for use with the locking mechanism.
Figure 24:
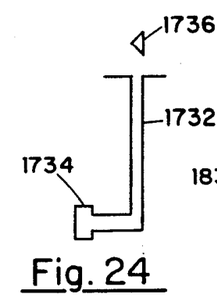
Figure 25:
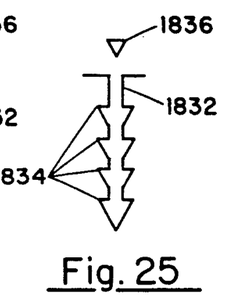
Figure 26:
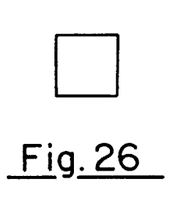
FIGS. 26 to 30 depict possible cross-sectional shapes of syringe bodies to be equipped with the locking needle assembly.
Figure 27:
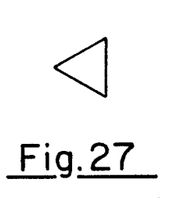
Figure 28:
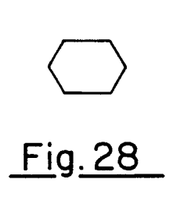
Figure 29:
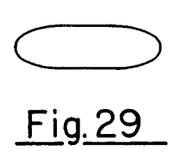
Figure 30:
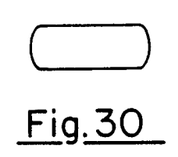

Push-on locking engagements may be used instead of the screw-on engagements of the previous embodiments. Some various push-on embodiments are illustrated in FIGS. 23 to 25. Catches 1636, 1736 and 1836 engage grooves 1632, 1732 and 1832, respectively Grove 1732 is somewhat different as it comprises a push and twist track, as compared to the push only tracks of FIGS. 23 and 25. Upon reaching catch spaces 1634, 1734 and 1834 catches 1636, 1736 and 1836, respectively, may not be retracted and locking is achieved.

It is contemplated that the locking needle mechanisms illustrated in FIGS. 13 to 25 can be used with a locking syringe such as that illustrated in FIGS. 1 to 12. While FIGS. 1 to 12 illustrate an oval syringe and FIGS. 13 to 25 illustrate a round syringe, other cross-sections, some of which are illustrated in FIGS. 26 to 30, are applicable. Naturally, the plunger will conform to the syringe shape in order to provide the proper sealing with respect to the interior walls of the syringe.

Figure 31:
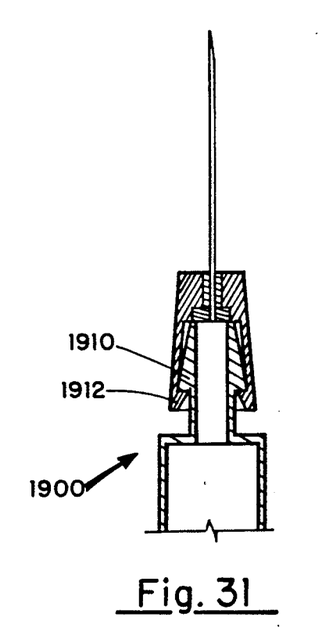
FIG. 31 depicts yet another needle locking assembly.

Another needle locking mechanism comprising an annular locking ramp 1910, and a continuous annular or a segmented catch 1912 on the syringe 1900 is illustrated in FIG. 31.

Figure 32:
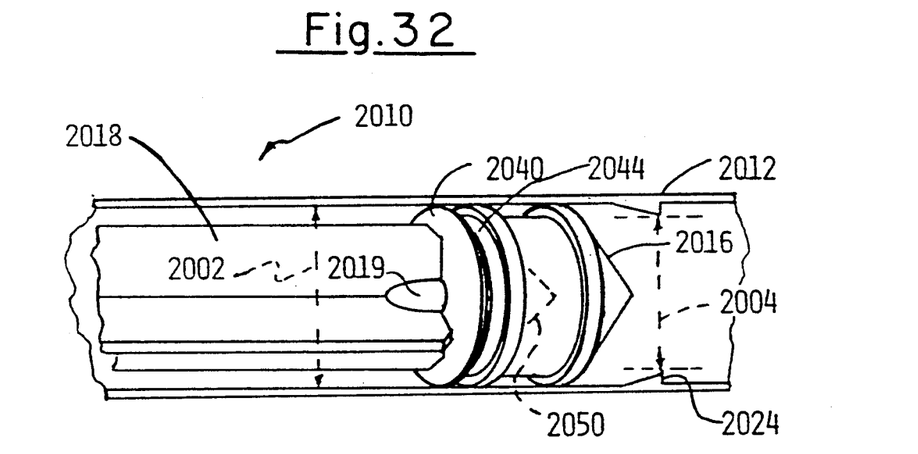
FIG. 32 is a perspective view of a plunger/driver, in a cut-away syringe body, depicting an alternate embodiment of a non-reusable syringe.
Figures 33, 34:
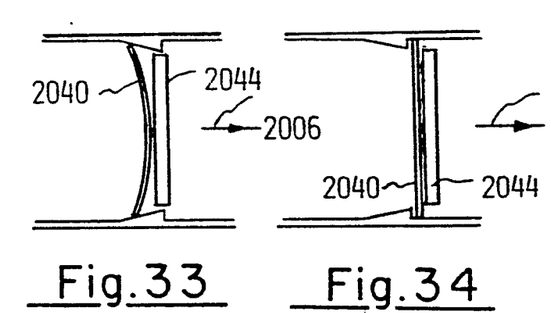
FIGS. 33 to 35 schematically depict the engagement of the driver with the locking means of the FIG. 32 embodiment.
Figure 35:
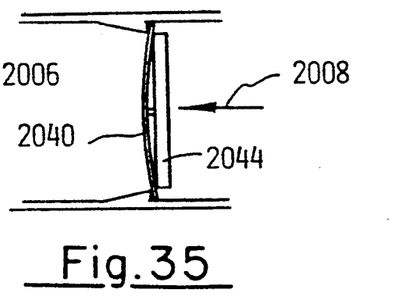

An alternate embodiment 2010 of the plunger/driver for a non-reusable syringe is drawn to the use of differing sized disks, wherein a thin rear disk 2040 has a diameter corresponding to the internal diameter 2002 of the syringe 2012 and a thick forward disk 2044 that has a smaller diameter, corresponding to the internal diameter 2004 of the syringe defined by locking stops 2024 forming a constriction in the internal diameter. Driver 2018, reinforcement portion 2019, support body 2030, disk 2040, and disk 2044 may be made in a single molded member. The smaller forward disk is of greater thickness than the rear disk and thus substantially inflexible compared to the rear disk 2040. This embodiment is illustrated in FIG. 32. As the plunger/driver advances in the direction of arrow 2006 as illustrated diagrammatically in FIGS. 33 and 34, disk 2044 is able to move (FIG. 33) past the locking stops 2024 without hindrance, however, the thinner and, accordingly, flexible disk 2040 deforms upon passage through the locking stops as shown in FIG. 33 and then returns to an undeformed shape after passing through the stops, as shown in FIG. 34. The thicker disk 2044 is substantially inflexible and is positioned sufficiently close to disk 2040 to prevent disk 2040 from flexing in a manner that would allow the disks to pass through the locking stops in the reverse direction indicated by arrow 2008.

While an illustrative embodiment of the invention has been described above, it is, of course, understood that various modifications will be apparent to those of ordinary skill in the art. Such modifications are within the spirit and scope of the invention, which is limited and defined only by the appended claims.

What is claimed is:

1. A syringe comprising:
   a) a body portion with an inner surface defining a volume for holding a fluid;
   b) a plunger conforming to the inner surface of said body portion so as to fit tightly and to form a seal separating the volume on either side of said plunger within said body portion;
   c) a driver onto which said plunger is secured, said plunger being positioned within said body portion and said driver extending out of said body portion through an opening in said boy portion at one end;
   d) a needle support means positioned at the end of said body portion opposite the end through which said driver extends, said needle support means defining a channel allowing the transfer of fluid within said boy portion to a needle or needle assembly mounted on said needle support;
   e) syringe locking means located on the inner surface of said body portion; and
   f) syringe engagement means adapted to matingly engage said syringe locking means, said engagement means being associated with said driver, separate from said plunger and advanceable towards said needle support, and over said locking means, and being retained at the needle support end of said body portion upon the engagement of said locking means, said engagement coinciding with fluid, initially present in the volume defined by said body portion, being substantially discharged, wherein said engagement means comprises adjacent first and second members, said first and second members being positioned such that said first member prevents said second member from flexing sufficiently to return over said syringe locking means after 2. A syringe as claimed in claim 1, wherein said locking means comprises complementary locking structures on said needle support and said needle assembly.

3. A syringe as claimed in claim 2, wherein said complementary locking structures comprise at least one groove, communicating with at least one associated catch space and at least one catch.

4. A syringe as claimed in claim 3, wherein said at least one groove is in the nature of a thread and engagement of said needle support with said needle assembly requires rotation of said needle assembly with respect to said needle support.

5. A syringe as claimed in claim 3, wherein said at least one catch is wedge-shaped with a flat face and positioned such that when said catch enters said groove a leading edge enters first and said flat face is perpendicular to walls of said groove and enters said groove last.

6. A syringe as claimed in claim 1, wherein said needle support is cylindrical with an outside diameter, said needle assembly has an inner and outer diameter where said needle assembly engages said needle support and said syringe further comprises a securing collar, coaxial with said needle support, having an inner diameter substantially similar to said outside diameter of said needle assembly.

7. A syringe as claimed in claim 6, wherein said locking means comprises complimentary structures on said needle assembly and said securing collar.

8. A syringe as claimed in claim 7, wherein said complementary locking structures comprise at least one groove communicating with at least one associated catch space and at least one catch.

9. A syringe as claimed in claim 1, wherein said syringe locking means comprises ramped surface locking stops on said inner surface of said body portion forming a construction and said adjacent first and second members associated with said driver comprise a larger diameter member that flexes to pass through said constriction and a smaller diameter, thicker second member, capable of passing through said constriction without deformation, said thicker second member positioned adjacent to said larger diameter member such that said larger diameter member may not flex in a manner that would allow a return passage of said adjacent first and second members through said constriction.

10. A locking needle assembly and syringe combination as claimed in claim 9 wherein said smaller, thicker second disk associated with said driver is positioned closer to said plunger than said larger diameter disk and therefore passes said ramped surface locking stops before said larger diameter disk upon discharge of fluid from said syringe.

11. A locking needle and syringe combination as claimed in claim 1, wherein said non-reusable syringe further comprises:
   a) a tubular member forming the body portion of said syringe defining a volume bounded by said tubular member's interior surface;
   b) a plunger configured and dimensioned to fit tightly within said tubular member contacting the interior surface of said tubular surface in a manner to form a seal separating the volume on one side of said plunger from the volume on the other side of said plunger within the tubular member, said plunger capable of movement within said tubular member;
   c) a one-piece driver affixed to said plunger, said driver extending out of an open end of said tubular member housing said plunger;
   d) needle support means positioned at the end of said tubular member opposite the end through which the driver extends, said needle support means defining a channel in communication with the interior volume of said tubular member through which fluid may be drawn into or expelled from the volume within said tubular member by movement of the driver and attached plunger within said tubular member;
   e) locking means comprising a plurality of ramp stops on said interior surface of said tubular member, said ramp stops being flush with said interior surface and rising above said interior surface with the raised portion of said ramp stops being closer to the needle support means that the flush end of said ramp stops; and
   f) engagement means comprising two ratchet members, on said driver, advanceable towards said needle support means over said ramp stops, formed in a manner such that said engagement means are being retained in the advanced position after passing over said ramp stops and prevent the withdrawal of said driver and plunger.

12. A syringe as in claim 11, wherein said two ratchet members are separate from said plunger and each comprise a first and a second substantially planar member with a plurality of slots in order to render said planar members more flexible.

13. A locking needle assembly and syringe comprising:
   a) a non-reusable syringe comprising a cylindrical needle support;
   b) a needle assembly comprising a cylindrical body configured, proportioned and dimensioned to matingly engage said needle support;
   c) a hypodermic needle permanently fixed to said needle assembly such that a hollow interior in said needle communicates with a hollow interior of said cylindrical body of said needle assembly; and
   d) a mechanical needle assembly locking means comprising complementary locking structures on said syringe and said needle assembly, wherein said complementary structures comprise;
      i) at least one groove communicating with at least one associated catch space; and
      i) at least one wedge-shaped catch.

14. A locking needle assembly and syringe combination as claimed in claim 13, wherein said at least one groove is in the nature of a thread and engagement of said needle support with said needle assembly requires rotation of said needle assembly with respect to said needle support.

15. A locking needle assembly and syringe combination as claimed in claim 13, wherein said syringe further comprises a securing collar, coaxial with said needle support, having an inside diameter substantially similar to an outside diameter of said needle assembly body.

16. A locking needle assembly and syringe combination as claimed in claim 15, wherein said locking means comprises complementary locking structures on said needle assembly and said securing collar.

17. A locking needle assembly and syringe combination as claimed in claim 14, wherein said at least one groove has a plurality of associated catch spaces positioned along said groove such that the combination with said at least one wedge-shaped catch results in a ratchet and pawl arrangement.

18. A hypodermic syringe and needle assembly comprising:
   a) a tubular member, forming the body portion of said syringe, defining a volume and having a non-circular cross-section, said tubular member having an interior surface;
   b) a rubber-type plunger, in cross-section, the perimeter of which bears sealingly with the interior surface of said tubular member when inserted into and moved within said tubular member;
   c) a driver affixed to said plunger, said driver extending out of an open end of said tubular member housing said plunger, said plunger configured and dimensioned to contact said interior surface of said tubular member in a manner that prevents rotation of said plunger within said tubular member;
   d) needle support means positioned at the end of said tubular ember opposite the end through which the driver extends, said needle support means containing a channel through which fluid may be drawn into or expelled from the volume within said tubular member by movement of the driver and attached plunger within said tubular member; and
   e) syringe locking means comprising a plurality of ramp stops on said interior surface of said tubular member, said ramp stops being substantially flush with said interior surface and rising above said interior surface with the raised portion of said ramp stops being closer to the needle support means than a substantially flush end of said ramp stops;

f) engagement means on said driver, separate from said plunger and advanceable towards said needle support means over said ramp stops, said engagement means being retained in the advanced position after passing over said ramp stops and preventing the withdrawal of said driver and plunger, wherein said engagement means comprises closely spaced first and second substantially planar members wherein the intervening space between said first and second substantially planar members is insufficient to allow said second planar member to flex sufficiently to return over said syringe locking means after having advanced over said locking means;

g) a needle assembly comprising a cylindrical body configured and dimensioned to matingly engage said needle support means;

h) a hypodermic needle permanently fixed to said needle assembly such that a hollow interior in said needle communicates with a hollow interior of said cylindrical body of said needle assembly; and i) a mechanical needle assembly locking means comprising complementary locking structures on said needle support means and said needle assembly, wherein said complementary structures comprise;
  i) at least one groove communicating with at least one associated catch space; and
  ii) at least one wedge-shaped catch.

19. A syringe as claimed in claim 18, wherein said syringe locking means comprises ramped surface locking stops on said inner surface of said body portion forming a constriction and said two planar members associated with said driver comprise a larger diameter disk that flexes to pass through said constriction and a smaller, thicker second disk, capable of passing through said constriction without deformation, positioned adjacent to said larger diameter disk such that said larger diameter disk may not flex in a manner that would allow a return passage of said double disk means through said constriction.

* * * * *